United States Patent
Sayani et al.

(10) Patent No.: US 11,621,062 B2
(45) Date of Patent: Apr. 4, 2023

(54) SECURE MEDICAL ALERT AND MEDICAL REFERRAL DELIVERY USING A CLOUD COMPUTING SERVER IN AN ONLINE/OFFLINE MODE

(71) Applicant: The Aga Khan University, Karachi (PK)

(72) Inventors: Saleem Sayani, Wynnewood, PA (US); Muhammad Abdul Muqeet, Karachi (PK); Hafsa Talat, Karachi (PK); Salik Sadruddin Merani, Karachi (PK); Muhammad Umair Khan, Karachi (PK)

(73) Assignee: The Aga Khan University, Karachi (PK)

( * ) Notice: Subject to any disclaimer, the term of this patent is extended or adjusted under 35 U.S.C. 154(b) by 0 days.

(21) Appl. No.: 16/573,896

(22) Filed: Sep. 17, 2019

(65) Prior Publication Data

US 2021/0027869 A1 Jan. 28, 2021

(30) Foreign Application Priority Data

Jul. 26, 2019 (PK) .................................... 523/2019

(51) Int. Cl.
| | |
|---|---|
| *G16H 10/60* | (2018.01) |
| *G16H 40/67* | (2018.01) |
| *G06K 7/14* | (2006.01) |
| *H04L 9/40* | (2022.01) |
| *G16H 30/20* | (2018.01) |

(52) U.S. Cl.
CPC .......... *G16H 10/60* (2018.01); *G06K 7/1417* (2013.01); *G16H 30/20* (2018.01); *G16H 40/67* (2018.01); *H04L 63/0428* (2013.01)

(58) Field of Classification Search
None
See application file for complete search history.

(56) References Cited

U.S. PATENT DOCUMENTS

| | | | |
|---|---|---|---|
| 7,908,155 B2 | 3/2011 | Fuerst et al. | |
| 2005/0144041 A1* | 6/2005 | Essig | G06Q 50/22 |
| | | | 705/2 |

(Continued)

FOREIGN PATENT DOCUMENTS

| | | | | |
|---|---|---|---|---|
| CN | 203376776 | | 1/2014 | |
| CN | 110462654 A | * | 11/2019 | ............. G06F 16/00 |

OTHER PUBLICATIONS

Tijan E, Aksentijević S, Ivanić K, Jardas M. Blockchain Technology Implementation in Logistics. Sustainability. 2019; 11(4):1185. https://doi.org/10.3390/su11041185 (Year: 2019).*

(Continued)

*Primary Examiner* — Lena Najarian
(74) *Attorney, Agent, or Firm* — Fish & Richardson P.C.

(57) ABSTRACT

A method for providing secure medical alerts includes executing, using a mobile healthcare worker application executing on a mobile healthcare worker device, a Health Level 7 (HL7) compliant protocol to retrieve medical profiles from a cloud computing server. Using the mobile healthcare worker application, a medical profile of a person (e.g., child or child's mother) is identified from the medical profiles when the mobile healthcare worker device is disconnected from the cloud computing server. The identifying includes reading, using a quick response (QR) code scanner, a QR code of an immunization document of the person, or capturing, using a biometric sensor, biometric data of the person. Using the medical profile of the person, an alert is generated indicating a medical deadline for the person on a graphical user interface of the mobile healthcare worker device when the mobile healthcare worker device is disconnected from the cloud computing server.

17 Claims, 5 Drawing Sheets

(56) References Cited

U.S. PATENT DOCUMENTS

| | | | |
|---|---|---|---|
| 2009/0216563 A1* | 8/2009 | Sandoval | G06Q 50/24 705/3 |
| 2013/0123667 A1* | 5/2013 | Komatireddy | A61B 5/0002 600/595 |
| 2014/0122125 A1* | 5/2014 | Deshpande | G06F 19/3418 705/3 |
| 2015/0120315 A1 | 4/2015 | Dann et al. | |
| 2015/0347692 A1 | 12/2015 | Bchihalouk et al. | |
| 2017/0085691 A1* | 3/2017 | Kim | H04M 1/27453 |
| 2017/0161439 A1* | 6/2017 | Raduchel | G06Q 10/063 |
| 2018/0167200 A1* | 6/2018 | High | A61B 5/1171 |
| 2018/0227119 A1* | 8/2018 | Bibera | H04L 9/3239 |
| 2018/0342321 A1 | 11/2018 | Bayne | |
| 2019/0205773 A1* | 7/2019 | Ackerman | G06F 21/6227 |
| 2019/0268165 A1* | 8/2019 | Monica | H04L 9/3236 |

OTHER PUBLICATIONS

Ahuja et al., "A Survey of the State of Cloud Computing in Healthcare", Network and Communication Technologies, Aug. 2012, 1(2):12-19.

Balestra, "Electronic Health Records: Patient Care and Ethical and Legal Implications for Nurse Practitioners", The Journal for Nurse Practitioners, Feb. 2017, 13(2):105-111.

Li et al., "Scalable and Secure Sharing of Personal Health Records in Cloud Computing Using Attribute-Based Encryption", IEEE Transactions on Parallel and Distributed Systems, Jan. 2013, 24(1):131-143.

Ma et al., "Intelligent Healthcare Systems Assisted by Data Analytics and Mobile Computing", Wireless Communications and Mobile Computing, Jul. 2018, 17 pages.

PatientGain [online], "Secure Cloud Based Apps For Healthcare Clinics & Organizations", retrieved on Nov. 12, 2020, retrieved from URL: https://www.patientgain.com/secure-cloud-based-apps-for-healthcare-clinics-organizations, 6 pages.

PatientNow [online], "Cloud vs Offline System", retrieved on Nov. 12, 2020, retrieved from URL: https://www.patientnow.com/cloud-vs-offline-system/, 2 pages.

PK Office Action in Pakistani Application No. 523/2019, dated Aug. 24, 2020, 2 pages.

Stantchev et al., "Cloud Computing Based Systems for Healthcare", The Scientific World Journal, 2014, 74 pages.

* cited by examiner

Execute, using a mobile healthcare worker application executing on a mobile healthcare worker device, a Health Level 7 (HL7) compliant protocol to receive a plurality of medical profiles from a cloud computing server when the mobile healthcare worker device is communicatively coupled to the cloud computing server over a communications network
504

Identify, using the mobile healthcare worker application, a medical profile of a child from the plurality of medical profiles when the mobile healthcare worker device is disconnected from the cloud computing server, the identifying comprising at least one of: reading, using a quick response (QR) code scanner, a QR code of an immunization document of the child, or capturing, using a biometric sensor, biometric data of the child
508

Generate, using the medical profile of the child, an immunization alert indicating an immunization deadline for the child on a graphical user interface of the mobile healthcare worker device when the mobile healthcare worker device is disconnected from the cloud computing server
512

FIG. 5

SECURE MEDICAL ALERT AND MEDICAL REFERRAL DELIVERY USING A CLOUD COMPUTING SERVER IN AN ONLINE/OFFLINE MODE

RELATED APPLICATION

This disclosure claims priority to Pakistan Patent Application No. 523/2019, entitled "Secure Medical Alert and Medical Referral Delivery Using a Cloud Computing Server in an Online/Offline Mode" and filed on Jul. 26, 2019, the entire contents of which are incorporated herein by reference.

TECHNICAL FIELD

The subject matter described herein relates to providing secure medical notifications indicating a medical deadline for a child or a mother of a child using a cloud computing server in an online/offline mode.

BACKGROUND

Emphasis is often laid on improving maternal and child health in low-income and middle-income countries. However, providing early childhood healthcare remains a problem in low-income and middle-income countries. Problems experienced with health service delivery and policy can lead to deteriorating Maternal, Newborn and Child Health (MNCH) outcomes, especially in remote and rural areas.

SUMMARY

In one aspect, a cloud computing system for providing secure medical alerts includes a cloud computing server and a mobile healthcare worker device. The cloud computing server includes one or more software development kits and one or more web modules configured to receive a request for multiple medical profiles. An application programming interface is configured to enable one or more controllers to retrieve the multiple medical profiles. The mobile healthcare worker device includes a biometric sensor configured to capture biometric data of a child when the mobile healthcare worker device is disconnected from the cloud computing server. A mobile healthcare worker application executes on the mobile healthcare worker device. The mobile healthcare worker application is configured to execute a Health Level 7 (HL7) compliant protocol to retrieve the multiple medical profiles when the mobile healthcare worker device is communicatively coupled to the cloud computing server over a communications network. Using the biometric data, a medical profile of the child is identified from the multiple medical profiles when the mobile healthcare worker device is disconnected from the cloud computing server. Using the medical profile of the child or a mother an alert is generated indicating a medical deadline for the child or a mother of the child on a graphical user interface of the mobile healthcare worker device.

In some variations, one or more of the following can be implemented either individually or in any feasible combination. A peer-to-peer blockchain network stores the multiple medical profiles. The peer-to-peer blockchain network executes inter-peer communication to validate new medical profiles added to the multiple medical profiles. The mobile healthcare worker application is further configured to access a cryptographic key stored on the cloud computing server. The cryptographic key is associated with a geographical area corresponding to the multiple medical profiles. Using the cryptographic key, the multiple medical profiles are retrieved from the peer-to-peer blockchain network.

In some variations, the biometric sensor includes a camera configured to capture a fingerprint of the child or a mother, a fingerprint sensor configured to capture the fingerprint of the child or a mother, a retina scanner configured to capture a retina scan of the child or a mother, or an iris scanner configured to capture an iris scan of the child or a mother.

In some variations, the mobile healthcare worker device further includes a quick response (QR) code scanner configured to read a QR code of an immunization document of the child.

In some variations, the mobile healthcare worker application is further configured to generate, using the graphical user interface of the mobile healthcare worker device, the medical profile of the child or a mother when the mobile healthcare worker device is disconnected from the cloud computing server. The medical profile of the child or a mother includes demographic data and health data of the child or a mother. A database entity link is transmitted between the medical profile of the child or a mother and an aggregate medical profile of individuals related to the child when the mobile healthcare worker device is communicatively coupled to the cloud computing server over the communications network.

In some variations, the mobile healthcare worker application is further configured to initiate an audio-visual telemedicine session with a primary care provider application executing on a primary care provider device when the mobile healthcare worker device is communicatively coupled to the primary care provider device over the communications network.

In some variations, the mobile healthcare worker application is further configured to retrieve a record of a number of vaccinations and a type of the vaccinations in stock within a geographical area corresponding to the multiple medical profiles when the mobile healthcare worker device is communicatively coupled to the cloud computing server over the communications network. Using the graphical user interface of the mobile healthcare worker device, a display is generated of the record of the number of vaccinations and the type of the vaccinations.

In some variations, a primary care provider application executes on a primary care provider device. The primary care provider application is configured to identify a medical specialist corresponding to a medical condition of the child or a medical condition of an individual related to the child. A database entity link is transmitted between the medical specialist and the medical profile of the child to the cloud computing server.

In another aspect, a method is described that includes executing, using a mobile healthcare worker application executing on a mobile healthcare worker device, a Health Level 7 (HL7) compliant protocol to retrieve multiple medical profiles from a cloud computing server when the mobile healthcare worker device is communicatively coupled to the cloud computing server over a communications network. Using the mobile healthcare worker application, a medical profile of a child is identified from the retrieved medical profiles when the mobile healthcare worker device is disconnected from the cloud computing server. The identifying includes at least one of reading, using a QR code scanner, a QR code of an immunization document of the child, or capturing, using a biometric sensor, biometric data of the child. Using the medical profile of the child, an alert is generated indicating a medical deadline for the child or a mother of the child on a graphical user interface of the mobile healthcare worker device when the mobile healthcare worker device is disconnected from the cloud computing server.

In some variations, one or more of the following can be implemented either individually or in any feasible combination. Using a peer-to-peer blockchain network, the multiple medical profiles are stored. The peer-to-peer blockchain network executes inter-peer communication to validate new medical profiles added to the multiple medical profiles. Using the mobile healthcare worker application, a cryptographic key stored on the cloud computing server is accessed. The cryptographic key is associated with a geographical area corresponding to the multiple medical profiles. Using the cryptographic key, the multiple medical profiles are retrieved from the peer-to-peer blockchain network.

In some variations, the biometric sensor includes a camera configured to capture a fingerprint of the child, a fingerprint sensor configured to capture the fingerprint of the child, a retina scanner configured to capture a retina scan of the child, or an iris scanner configured to capture an iris scan of the child.

In some variations, using the graphical user interface of the mobile healthcare worker device, the medical profile of the child is generated when the mobile healthcare worker device is disconnected from the cloud computing server. The medical profile of the child includes demographic data and health data of the child. Using the mobile healthcare worker application, a database entity link is transmitted between the medical profile of the child and an aggregate medical profile of individuals related to the child when the mobile healthcare worker device is communicatively coupled to the cloud computing server over the communications network.

In some variations, using the mobile healthcare worker application, an audio-visual telemedicine session is initiated with a primary care provider application executing on a primary care provider device when the mobile healthcare worker device is communicatively coupled to the primary care provider device over the communications network.

In some variations, using the mobile healthcare worker application, a record is retrieved of a number of vaccinations and a type of the vaccinations in stock within a geographical area corresponding to the multiple medical profiles when the mobile healthcare worker device is communicatively coupled to the cloud computing server over the communications network. Using the graphical user interface of the mobile healthcare worker device, a display is generated of the record of the number of vaccinations and the type of the vaccinations.

In some variations, using a primary care provider application executing on a primary care provider device, a medical specialist is identified corresponding to a medical condition of the child or a medical condition of an individual related to the child. Using the primary care provider application, a database entity link is transmitted between the medical specialist and the medical profile of the child to the cloud computing server.

The subject matter described herein can provide many advantages. For example, the mobile healthcare worker application can be designed to be used by healthcare workers and persons administering healthcare (e.g., immunizations) to infants, children, or mothers in low-income and middle-income countries during community visits or within the premises of health facilities. The mobile healthcare worker application can improve the quality, coverage, and access to child healthcare (e.g., immunization) and maternal healthcare services using digitization of health and identity data and the cloud computing server. The mobile healthcare worker application can address the monitoring and improving of health outcomes for an entire geographically dispersed family (individuals related to the child) by maintaining a separate aggregate profile containing the health record of each individual as well as an aggregate medical profile of individuals related to the child. The two profiles can be linked on the cloud computing server for medical diagnosis. The healthcare and identity profiles can be searched through a family number, a cellular phone number, an immunization card number, fingerprints, or QR codes, etc.

The mobile healthcare worker application or a separate primary care provider application can access, from the cloud computing server, and display a graphical growth chart of a child, a nutritional record, or a sickness record. The mobile healthcare worker application can also access and display a comprehensive record of a stock of vaccinations with respect to a geographical area for healthcare workers. The mobile healthcare worker application and the primary care provider application in concert with the cloud computing server and the secure medical records database strengthen child and maternal healthcare, immunization results management, and the patient referral system. Moreover, the embodiments disclosed herein improve the capacity building of healthcare staff in low-income and middle-income countries through educational videos provided by the mobile healthcare worker application.

The details of one or more variations of the subject matter described herein are set forth in the accompanying drawings and the description below. Other features and advantages of the subject matter described herein will be apparent from the description, the drawings, and the claims.

BRIEF DESCRIPTION OF THE DRAWINGS

Like reference symbols in the various drawings indicate like elements.

DETAILED DESCRIPTION

Example Environment for Providing Secure Medical Notifications

Figure 1:
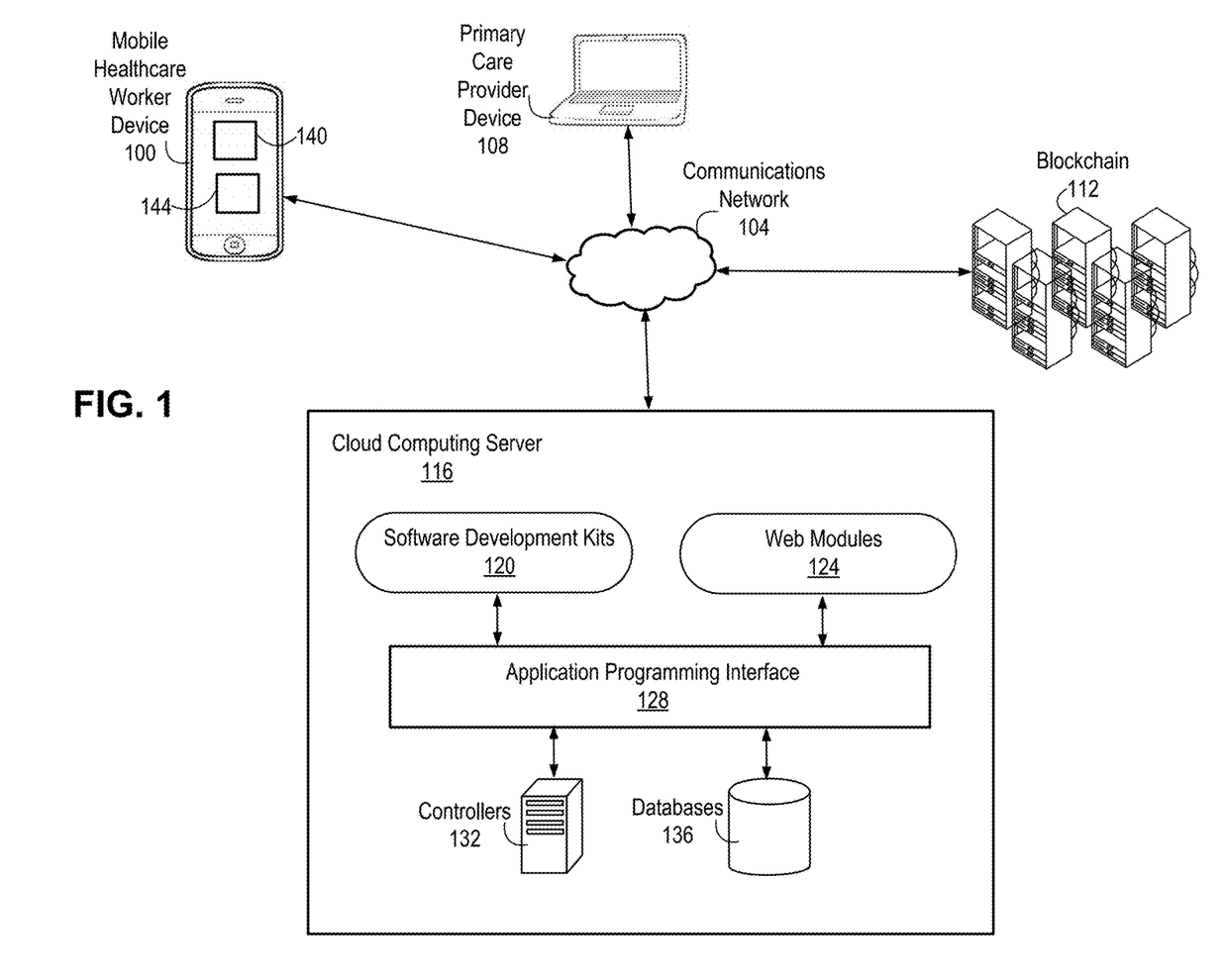
FIG. 1 illustrates an example environment for providing secure medical notifications and medical referrals using a cloud computing server in an online/offline mode.

FIG. 1 illustrates an example environment for providing secure medical notifications and delivering medical referrals using a cloud computing server 116 in an online/offline mode. The environment includes a mobile healthcare worker device 100, a primary care provider device 108, a blockchain 112, and the cloud computing server 116. Cloud computing is a model of service delivery for enabling convenient, on-demand network access to a shared pool of configurable computing resources (e.g. networks, network bandwidth, servers, processing resources such as the healthcare worker device 100, memory, cloud storage such as for encrypted keys, applications, virtual machines, and services). The healthcare worker device 100 and cloud computing services consumers are connected to the cloud computing server 116 through network links and network adapters. In other embodiments, the environment includes additional or fewer components than those described herein. Similarly, the functions can be distributed among the components or different entities in a different manner than is described here.

The mobile healthcare worker device 100 executes a mobile healthcare worker application in accordance with the cloud computing environment to provide secure medical notifications (e.g., for immunization, a medical procedure, a prescription refill, etc.). The mobile healthcare worker device 100 is a smartphone, tablet, laptop, a phablet, or another mobile device configured to execute the mobile healthcare worker application in accordance with the cloud computing environment. The mobile healthcare worker device 100 includes a biometric sensor 140 and a quick response (QR) code scanner 144. In other embodiments, the mobile healthcare worker device 100 includes additional or fewer components than those described herein. Similarly, the functions can be distributed among the components or different entities in a different manner than is described here. The mobile healthcare worker device 100 is implemented using the components illustrated and described in more detail with reference to FIG. 4 below.

The mobile healthcare worker application is designed to be used by healthcare workers (e.g., providing immunizations to children) during community visits in low-income and middle-income countries or within the premises of healthcare facilities. The mobile healthcare worker application improves quality, coverage, and access to child immunization and maternal healthcare services. For example, the immunizations targeted by the mobile healthcare worker application include OPV-O, HEP-B, BCG, OPV-1, Rota-1, PCVIO-1, Penta-1, OPV-2, Rota-2, PCVIO-2, Penta-2, OPV-3, IPV, PCVIO-3, Penta-3, Measles-1, and Measles-2. The mobile healthcare worker application addresses medical care needs of an entire family by maintaining a medical profile containing a health record of each individual as well as an aggregate medical profile of individuals related to the child. All data at rest and in transit is encrypted. The medical profiles can be retrieved using a family medical ID number, a national identity card (NIC) number, a phone number, an immunization card number, fingerprints, or a QR code. The mobile healthcare worker application can further provide a graphical display of a growth chart of a child or display a record of a stock of vaccinations with respect to a geographical area covered by a healthcare worker. The mobile healthcare worker application improves medical results management and patient medical referrals. Furthermore, the mobile healthcare worker application improves capacity building of healthcare staff in low- and middle-income countries by providing educational videos.

The mobile healthcare worker application provides a national-level solution for providing healthcare in remote areas. The mobile healthcare worker application enables secure communication between a patient, healthcare worker, and/or immunization provider in a community setting, and also serves as a way to improve governance and accountability (e.g., through the use of the blockchain 112). The mobile healthcare worker application places the patient at the center of the healthcare system, enabling immunization providers and/or healthcare workers to provide care to mother and child using the mobile healthcare worker device 100. The mobile healthcare worker application can connect in real time to a central health platform (e.g., on the cloud computing server 116) maintaining the patient's personal health records and family health records.

The biometric sensor 140 is configured to capture biometric data of a child when the mobile healthcare worker device 100 is disconnected from the cloud computing server 116. The capture function is performed, e.g., when a healthcare worker visits a family to provide social services, government assistance, or health-related services in a remote area of a low- to middle-income country, where internet or cellular services are limited. In some embodiments, the biometric sensor 140 includes a camera configured to capture a fingerprint of the child, a fingerprint sensor configured to capture the fingerprint of the child. The camera or fingerprint sensor measures a physical difference between ridges and valleys of the fingerprint. For example, an optical fingerprint sensor projects the irregular 3D fingerprint onto a 2D flat plane in the captured fingerprint image.

In some embodiments, the biometric sensor 140 includes a retina scanner configured to capture a retina scan of the child. The retina scanner transmits low-energy infrared light into the child's eye to trace a path on the retina. The mobile healthcare worker application executes on the mobile healthcare worker device 100. A pattern of variations of light reflections is digitized by the mobile healthcare worker application and compared against data in the medical profile. In some embodiments, the biometric sensor 140 includes an iris scanner configured to capture an iris scan of the child. A video camera of the mobile healthcare worker device 100 along with subtle near infrared illumination can be used to acquire an images of a structure of the iris of the child. The mobile healthcare worker application encodes a digital template from the resulting pattern to allow the identification of the child.

In some embodiments, the mobile healthcare worker device 100 includes the QR code scanner configured to read a QR code of an immunization document of the child. The immunization document is a vaccination card, a printed health report, an identity card, a health insurance card, or a government document. The mobile healthcare worker application reads the QR code including black squares arranged in a square grid on a white background, and processes the data using Reed-Solomon error correction until the image is interpreted. The mobile healthcare worker application extracts identity data from the patterns that are present in both horizontal and vertical components of the extracted image. In some embodiments, the mobile healthcare worker application updates an immunization record in a medical profile if the immunization document indicates the child has already been vaccinated at another location. The location where the vaccine was given (e.g., in a facility or outreach location), date, and other details can be stored.

The mobile healthcare worker application is configured to execute a Health Level 7 (HL7) compliant protocol to retrieve multiple medical profiles when the mobile healthcare worker device 100 is communicatively coupled to the cloud computing server 116 and/or blockchain 112 over the communications network 104. The retrieve function is performed, e.g., when a healthcare worker visits a government location, healthcare center, or other location that has internet or cellular service. The HL7 compliant protocol is a messaging standard enabling electronic data exchange in the clinical domain and allows secure exchange of clinical data between central patient care systems, distributed environments where data resides in departmental systems, healthcare information technology vendors, and healthcare providers (e.g., the primary care provider device 108). The HL7 compliant protocol supports a majority of medical information transmission interfaces used in the healthcare industry globally.

The mobile healthcare worker application is configured to identify, using the biometric data, a medical profile of the child from the multiple retrieved medical profiles when the mobile healthcare worker device 100 is disconnected from the cloud computing server 116, e.g., at the remote location. The medical profile of the child is identified using pattern matching and/or feature extraction and machine learning to match the captured biometric data of a child against stored biometric data in the medical profile. For example, the mobile healthcare worker application can perform a one-to-one comparison of a captured biometric with a specific template stored in the mobile healthcare worker device 100 in order to verify the identity of the child. Reference models for the population of a geographical area serviced by the healthcare worker can be generated and stored in the mobile healthcare worker device 100.

The primary care provider device 108 can be located at a hospital, a health clinic, a doctor's office, or any other facility providing primary medical care. The primary care provider device 108 executes a primary care provider application in accordance with the cloud computing environment to provide medical care, notifications, medical referral information, telemedicine, etc. The primary care provider device 108 can be a desktop computer, a smart computer monitor, a smart audio/visual projector, a smart medical device, or another non-mobile device configured to execute the primary care provider application in accordance with the cloud computing environment. The primary care provider device 108 can be implemented using the components illustrated and described in more detail with reference to FIG. 4 below.

The blockchain 112 can be a peer-to-peer computer or database network storing multiple medical profiles. The blockchain 112 includes a growing list of cryptographic medical records, called blocks, which are linked using cryptography. Each block includes a cryptographic hash of a previous block, a timestamp, and cryptographic transaction data. The blockchain 112 is typically managed by a peer-to-peer network collectively adhering to a protocol for inter-node communication and validating new blocks. Once recorded, the data in any given block cannot be altered retroactively without alteration of all subsequent blocks, which requires consensus of the network majority. The peer-to-peer blockchain network 112 can be implemented using the components illustrated and described in more detail with reference to FIG. 4 below.

The peer-to-peer blockchain network 112 stores a number of medical profiles (e.g., hundreds, thousands, tens of thousands or more) across distributed databases, servers, and local storage. The peer-to-peer blockchain network 112 executes inter-peer communication to validate new medical profiles added to the medical profiles. In some embodiments, when the mobile healthcare worker device 100 or the primary care provider device 108 adds data to a stored medical profile on the blockchain 112, creates a new medical profile, requests retrieval of multiple medical profiles, or requests a transaction involving a medical profile, the cloud computing server 116 causes an endorsement request message to be sent to each of multiple devices of the blockchain 112. Each of the multiple devices of the blockchain 112 is a potential member of a quorum for transactions involving that medical profile. The endorsement request message is configured to cause each of the multiple devices of the blockchain 112 to provide an endorsement of the requested transaction.

The mobile healthcare worker application is generally configured to access a cryptographic key stored on the cloud computing server 116 as part of the medical profile transaction process. The cryptographic key is associated with a geographical area corresponding to the multiple medical profiles, e.g., a postal code, a state, a neighborhood, a town, a city, or a district. The mobile healthcare worker application retrieves, using the cryptographic key, the multiple medical profiles from the peer-to-peer blockchain network 112. For example, when a device of the blockchain 112 receives a prompt for a transaction to be performed on a medical profile, the blockchain device 112 endorses the transaction. The blockchain device 112 signs an endorsement message using the cryptographic key and transmits the signed endorsement message to the cloud computing server 116. In some embodiments, a private key is stored within a secure enclave within the mobile healthcare worker device 100. A secure enclave in each mobile healthcare worker device 100 is thus used to store the private key and to generate a digital signature of that mobile healthcare worker device 100 for security verification with the cloud computing server 116 and the blockchain 112.

The cloud computing server 116 can include software development kits (SDKs) 120, web modules 124, an application programming interface (API) 128, one or more controllers 132 including one or more processors, and one or more databases 136 connected to the one or more controllers 132. At least one of the one or more SDKs 120 and the one or more web modules 124 can receive, from the mobile healthcare worker device 100 executing the mobile healthcare worker application, a request for medical profiles or medical records. The one or more SDKs 120 can receive images, requests, or other data from the mobile healthcare worker application when the mobile healthcare worker device 100 is a mobile phone, a tablet computer, or a phablet computer. The one or more web modules 124 can receive images or other data from the primary care provider device 108. The cloud computing server 116 is implemented using the components illustrated and described in more detail with reference to FIG. 4 below.

The API 128 can be a set of subroutine definitions, protocols, and/or tools that define protocols of communication between the mobile healthcare worker application and the cloud computing server 116 and between the client-application 118 and the computing server 116. The API 128 is configured to enable the one or more controllers 132 to retrieve the multiple medical profiles. The API 128 can ensure, for example, that the medical data or requests from the at least one of the one or more software development kits 120 and the one or more web modules 124 can be read by the one or more controllers 132 and the one or more processors.

Each database 136 can be a cloud database, which can advantageously permit an easy scalability of the database 136 when required (e.g., when additional data needs to be stored, which can happen, for example, when a number of mobile healthcare worker devices or primary care provider devices increase beyond a threshold value). In one implementation, access to the database 136 can be provided as a service. In some implementations, the database 136 can be run on virtual machine instances. In one implementation, the database 136 can be a disk storage. In some alternate implementations, the database 136 can be a main memory (e.g., random access memory) rather than a disk storage. In those alternate implementations, access of data from the main memory can advantageously eliminate seek time when querying the data, which can provides a faster access of data, as compared to accessing data from the disk.

The use of a cloud computing server 116 can be advantageous over a traditional server, as the cloud computing server 116 generally permits a quick scalability by addition of additional web services within in a few seconds. When the load on the mobile healthcare worker application or the primary care provider application increases, additional processors or databases 136 can be added-or alternately the processing abilities of the existing processors or databases 136 can be enhanced-within a few seconds. Additionally, inclusion of all of the one or more software development kits 120, one or more web modules 124, API 128, at least one data processor, and database 136 within the cloud computing server 116 can advantageously enable: a dynamic provisioning, monitoring and managing of the mobile healthcare worker application and the primary care provider application, as well as an easy and a quick (e.g., within a few seconds) restoring the mobile healthcare worker application and/or the primary care provider application to a previous version of those applications if and when required.

The communications network 104 includes networking resources (for example, networking equipment, nodes, routers, switches, and networking cables) that interconnect the mobile healthcare worker device 100, the primary care provider device 108, the blockchain 112, and the cloud computing server 116 and help facilitate access for the devices to cloud computing services. In an embodiment, the network 104 represents any combination of one or more local networks, wide area networks, or internetworks coupled using wired or wireless links deployed using terrestrial or satellite connections. Data exchanged over the network 104, is transferred using any number of network layer protocols, such as Internet Protocol (IP), Multiprotocol Label Switching (MPLS), Asynchronous Transfer Mode (ATM), Frame Relay, etc. Furthermore, in embodiments where the network 104 represents a combination of multiple sub-networks, different network layer protocols are used at each of the underlying sub-networks. In some embodiments, the network 104 represents one or more interconnected internetworks, such as the public Internet.

Example Graphical User Interface for a Mobile Healthcare Worker Application

Figure 2:
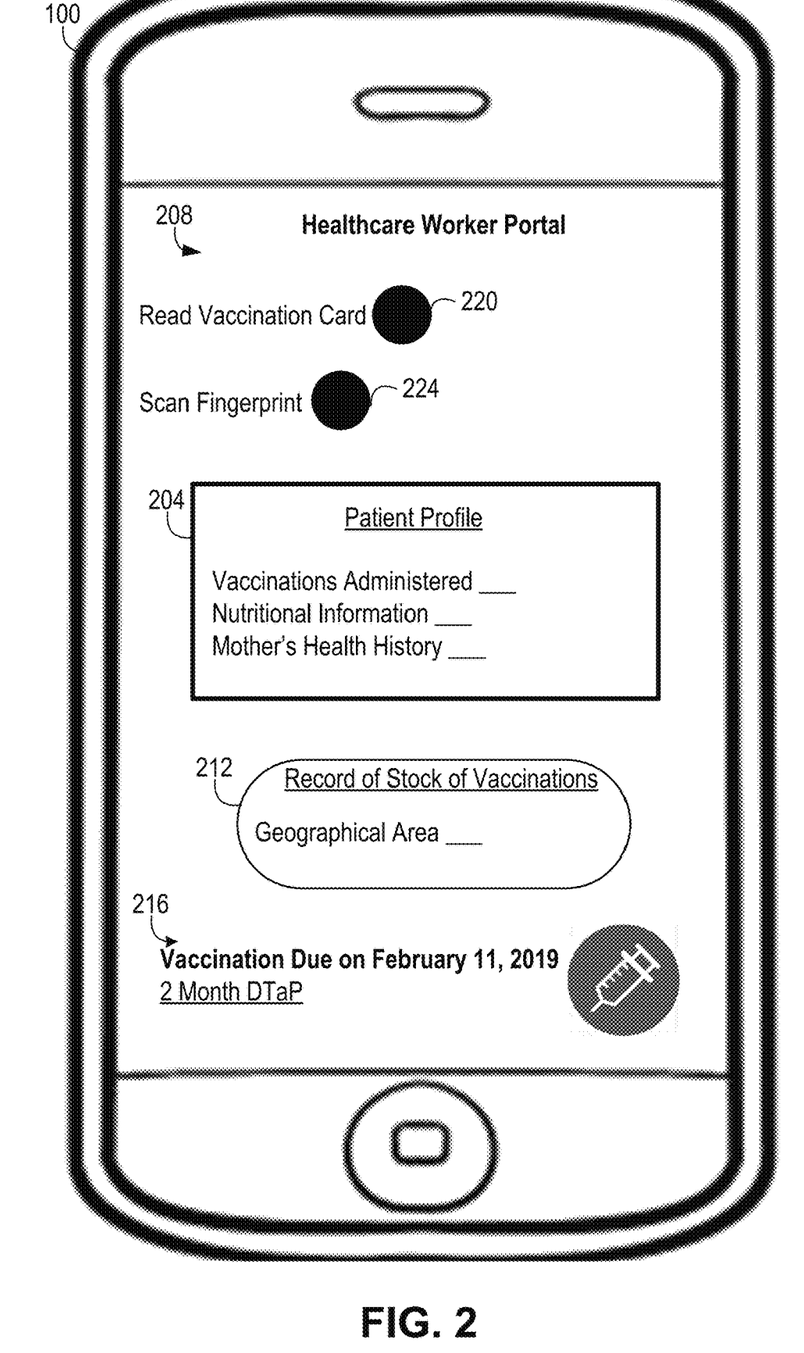
FIG. 2 illustrates an example graphical user interface for a mobile healthcare worker application for providing secure medical notifications using a cloud computing server in an online/offline mode.

FIG. 2 illustrates an example graphical user interface 208 for a mobile healthcare worker application for providing secure medical notifications using a cloud computing server 116 in an online/offline mode. The graphical user interface 208 is displayed on a screen of the mobile healthcare worker device 100 executing the mobile healthcare worker application. The graphical user interface 208 includes a computer-executable semantic icon 220, a computer-executable semantic icon 224, a patient medical profile entry window 204, a display 212 of a record of a stock of vaccinations, and an immunization alert 216. In other embodiments, the graphical user interface 208 includes additional or fewer components than those described herein. Similarly, the functions can be distributed among the components or different objects or graphics in a different manner than is described here.

The computer-executable semantic icon 224 is configured to activate the biometric sensor 140 (e.g., camera or fingerprint sensor) of the mobile healthcare worker device 100. The configured computer-executable semantic icon 224 thus enables capture of a fingerprint of a child. Similarly, the computer-executable semantic icon 220 is configured to activate the QR code sensor 144 of the mobile healthcare worker device 100. The configured computer-executable semantic icon 220 thus enables capture of a QR code of an immunization document of the child, as illustrated and described in more detail with reference to FIG. 1 above. The computer-executable semantic icons 220, 224 can be implemented using the components illustrated and described in more detail with reference to FIG. 4 below.

The mobile healthcare worker application is configured to track progress of pregnancy of a mother and notify a healthcare worker or parent regarding a deadline of the child's immunization or other medical procedure based on registered birth information using, e.g., color codes for alerts 216 if a deadline is near. The mobile healthcare worker application also enables an administrative network to responsively update the deadlines. The operation of the mobile healthcare worker application is beneficial in geographical areas having lower internet or network coverage. The mobile healthcare worker application generates the immunization alert 216 for the healthcare worker using the medical profile of the child. All data at rest and in transit is encrypted. The immunization alert 216 indicates an immunization deadline (e.g., Feb. 11, 2019, as shown in FIG. 2) for the child on the graphical user interface 208 of the mobile healthcare worker device 100. The immunization alert 216 can include the immunization deadline, the name or type of vaccine (e.g., DTaP, as shown in FIG. 2), as well as which immunization period the vaccine is for (e.g., 2 month, as shown in FIG. 2). The immunization alert 216 is generated by a vaccine recommendation engine running on the cloud computing server 116 or on the mobile healthcare worker device 100 as part of the mobile healthcare worker application. The vaccine recommendation engine uses data in the medical profile of the child, such as age, geographical location, medical history, available stock of vaccines 212, past history of vaccination, etc., to determine whether the immunization alert 216 should be generated.

The mobile healthcare worker application is further configured to retrieve a record of a number of vaccinations and a type of the vaccinations in stock within a geographical area. The geographical area (e.g., a postal code, city, village, health care center location, or other government unit) corresponds to the multiple medical profiles. The mobile healthcare worker application retrieves the record of the vaccinations stock when the mobile healthcare worker device 100 is communicatively coupled to the cloud computing server 116 over the communications network 104. The mobile healthcare worker application generates, using the graphical user interface 208 of the mobile healthcare worker device 100, a display 212 of the record of the number of vaccinations and the type of the vaccinations. For example, a number of doses of Vaccine A required for 2 weeks can be 80. The percentage required as a minimum stock is 25% (0.25). Thus, the minimum stock can be determined as 80×0.25 doses, or 20 doses. There should be at least 20 doses of Vaccine A in stock at the healthcare facility in the particular geographical area when the next supply of vaccine is collected.

In some embodiments, the mobile healthcare worker application is configured to generate, using the graphical user interface 208 of the mobile healthcare worker device 100, the medical profile of a child when the mobile healthcare worker device 100 is disconnected from the cloud computing server 116. This can happen, e.g., on a visit to the child's home or school in a geographical area having lower levels of internet or cellular coverage in a low-income or middle-income country. The medical profile of the child includes demographic data and health data of the child. A data entry window 204 on the graphical user interface 208 is used to enter data such as a list and dates of vaccinations administered to the child, nutritional information of the child, or a health or diagnostic history of the mother. The mobile as well as web-based embodiments disclosed herein thus deliver healthcare throughout the time span of childbirth including postnatal care services. The authenticity of the data is ensured since data entry is performed for specially trained staff.

The mobile healthcare worker application transmits a database entity link between the medical profile of the child and an aggregate medical profile of individuals related to the child when the mobile healthcare worker device 100 is communicatively coupled to the cloud computing server 116 or the blockchain 112 over the communications network 104. The database entity link is a schema object in the medical profile of the child that enables the mobile healthcare worker application or the primary care provider application to access objects in medical profiles of other family members. The health records of members of a family are thus tied together, such that illness or nutrition information can be shared and used to facilitate diagnosis. For example, the illness information can include diarrhea, breathing and cough disorders, fever, anemia, eye infection, presence of intestinal worms, or malaria. A child's maternal health history in the form of tables and views on another database can be used to improve health outcomes for the child.

In some embodiments, the mobile healthcare worker application is further configured to initiate an audio-visual telemedicine session with the primary care provider application. The audio-visual telemedicine session can be initiated with the primary care provider device 108, e.g., when the mobile healthcare worker device 100 is communicatively coupled to the primary care provider device 108 over the communications network 104. For example, a telemedicine session for remote patient monitoring, also known as telemonitoring, can be especially beneficial in low- and middle-income countries to enable patients with chronic diseases to be monitored in remote areas using mobile medical devices, e.g., that collect data about blood sugar levels, blood pressure or other vital signs. In some embodiments, the telemedicine session enables a healthcare worker to share patient information, such as lab results, with a physician at another location. The telemedicine session can allow a primary care provider or specialist to communicate in real time by the use of video conferencing software.

Example Graphical User Interface for a Primary Care Provider Application

Figure 3:
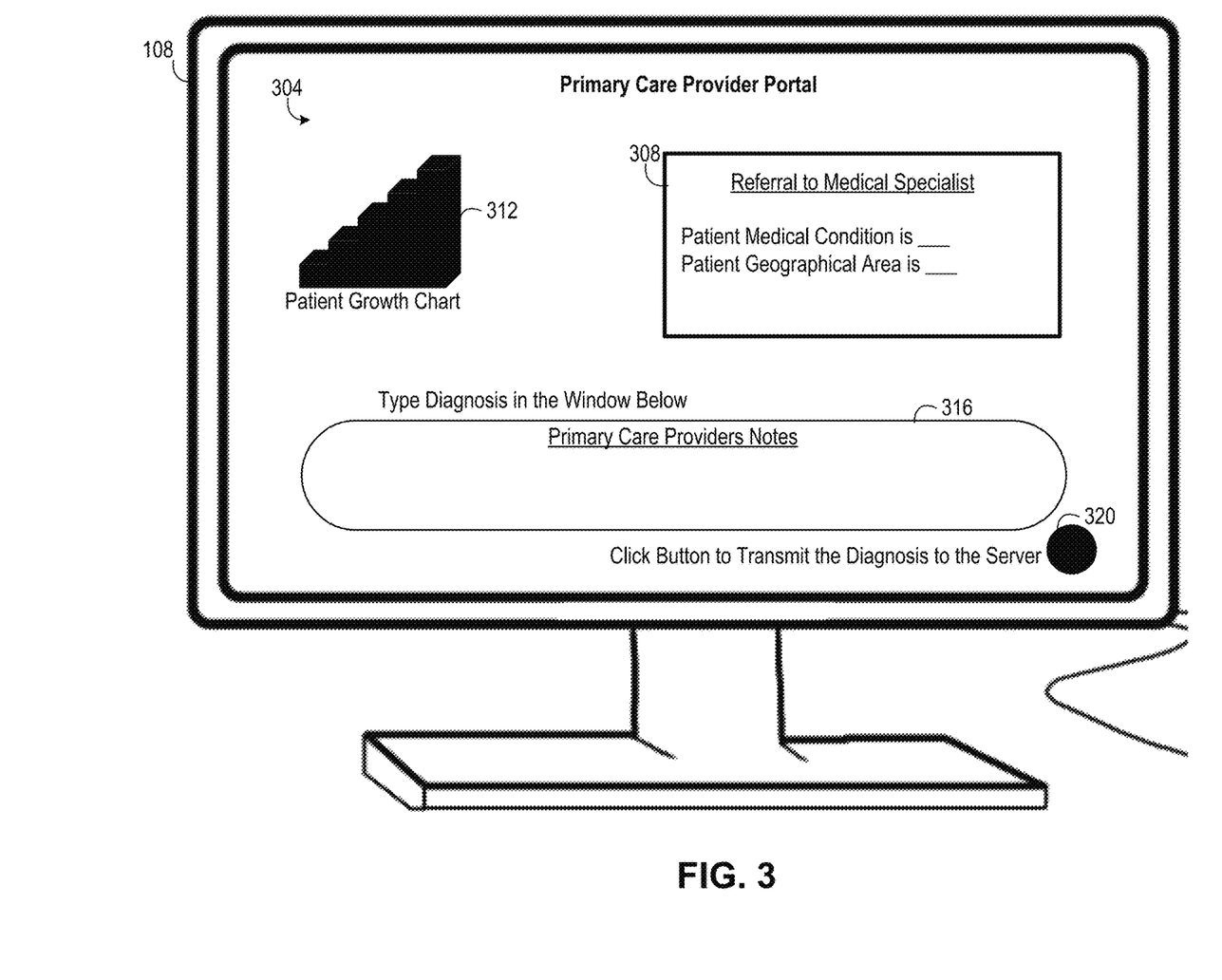
FIG. 3 illustrates an example graphical user interface for a primary care provider application for delivering medical referrals using a cloud computing server.

FIG. 3 illustrates an example graphical user interface 304 for a primary care provider application for delivering medical referrals 308 using a cloud computing server 116. The graphical user interface 304 is displayed on a screen of the primary care provider device 108 executing the primary care provider application. The graphical user interface 304 includes a medical specialist referral window 308, a computer graphic 312, a patient medical diagnosis entry window 316, and a computer-executable semantic icon 320. In other embodiments, the graphical user interface 304 includes additional or fewer components than those described herein. Similarly, the functions can be distributed among the components or different objects or graphics in a different manner than is described here.

The medical specialist referral window 308 is configured to generate, retrieve, or transmit secure medical specialist referrals for a child or adult patient. The primary care provider application is thus enabled to identify a medical specialist corresponding to a medical condition of the child or a medical condition of an individual related to the child, for example, anemia or hearing loss. In a low- or middle-income area, a medical specialist may be geographical far from the primary care provider or patient. A healthcare worker can therefore be required to follow up on the referral and provide assistance in obtaining the specialist care. The primary care provider application transmits a database entity link between the medical specialist and the medical profile of the child to the cloud computing server 116. All data at rest and in transit is encrypted. The mobile healthcare worker application can later retrieve the medical specialist referral securely before providing follow-up services. The functionality of the medical specialist referral window 308 provides transparency and secure medical data sharing among the mobile healthcare worker device 100, the primary care provider device 108, and the cloud computing server 116. All data at rest and in transit is encrypted. The benefits and advantages of the graphical user interface 304 thus include reducing communication-based problems associated with medical referrals. Thus, physicians are no longer left wondering whether a patient obtained needed care, prescriptions or tests.

The computer graphic 312 displays a growth chart of the child or other relevant graphical medical information for the primary care provider. The primary care provider application generates the computer graphic 312 based on medical information in the medical profiles retrieved from the cloud computing server 116 and/or blockchain 112. The patient medical diagnosis entry window 316 is used by the primary care provider to generate and transcribe diagnostic notes and information. The primary care provider application encodes the diagnostic notes and information and prepares them for secure delivery to the cloud computing server 116 and/or blockchain 112 by executing an HL7 compliant protocol. The computer-executable semantic icon 320 is configured to securely deliver medical information to the cloud computing server 116 and/or blockchain 112. The computer-executable semantic icons 220, 224 can be implemented using the components illustrated and described in more detail with reference to FIG. 4 below.

Example Machine for Providing Secure Medical Notifications

Figure 4:
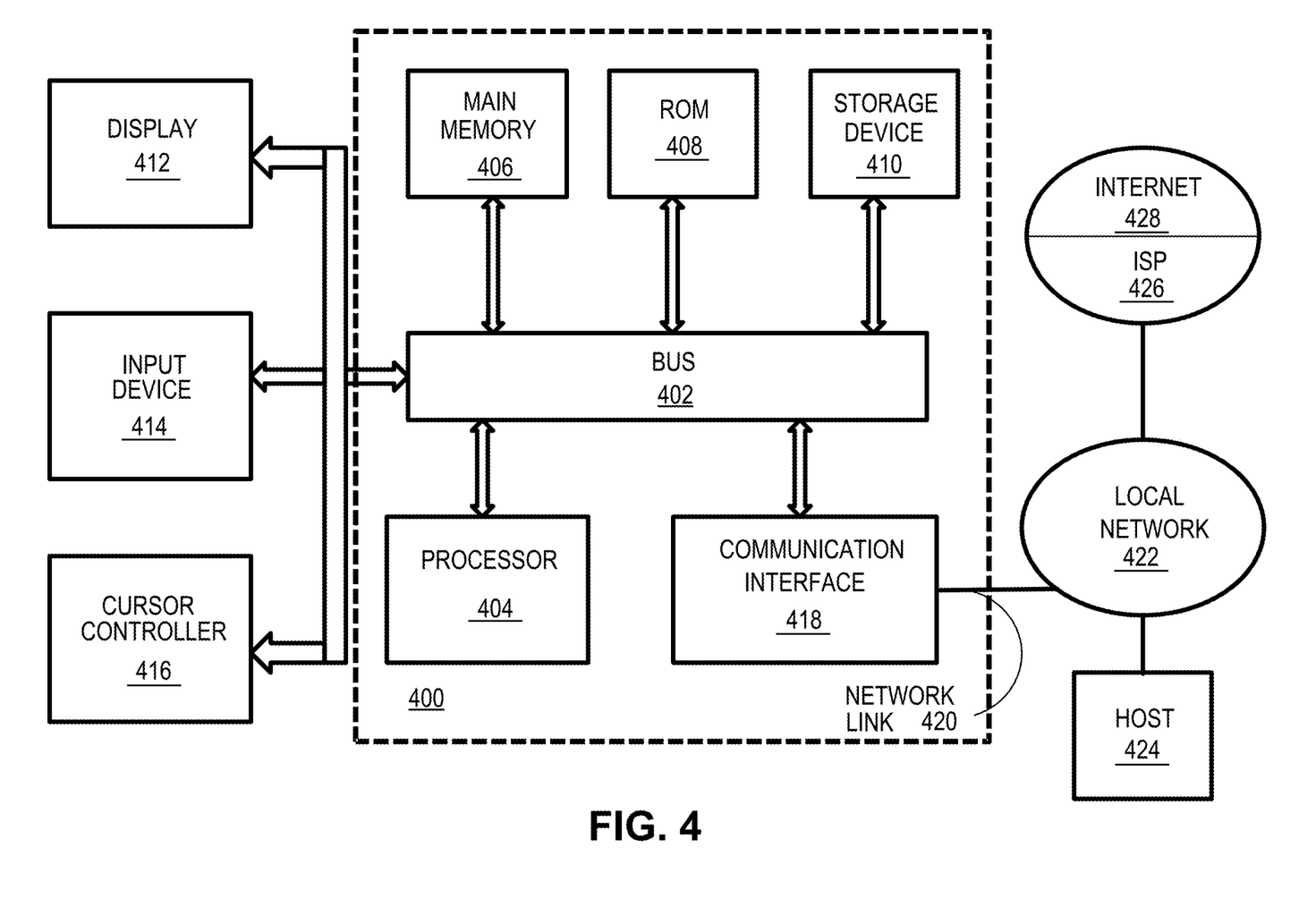
FIG. 4 illustrates an example machine for providing secure medical notifications and delivering medical referrals in an online/offline mode.

FIG. 4 illustrates an example machine 400 for providing secure medical notifications and delivering medical referrals in an online/offline mode. The mobile healthcare worker device 100, primary care provider device 108, cloud computing server 116, or elements of the blockchain 112 can be implemented as the computer system 400.

In an implementation, the computer system 400 is a special purpose computing device. The special-purpose computing device is hard-wired to perform the techniques or includes digital electronic devices such as one or more application-specific integrated circuits (ASICs) or field programmable gate arrays (FPGAs) that are persistently programmed to perform the techniques or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. In various embodiments, the special-purpose computing devices are desktop computer systems, portable computer systems, handheld devices, network devices or any other device that incorporates hard-wired and/or program logic to implement the techniques.

In an embodiment, the computer system 400 includes a bus 402 or other communication mechanism for communicating information, and a hardware processor 404 coupled with a bus 402 for processing information. The hardware processor 404 is, for example, a general-purpose microprocessor. The computer system 400 also includes a main memory 406, such as a random-access memory (RAM) or other dynamic storage device, coupled to the bus 402 for storing information and instructions to be executed by processor 404. In one implementation, the main memory 406 is used for storing temporary variables or other intermediate information during execution of instructions to be executed by the processor 404. Such instructions, when stored in non-transitory storage media accessible to the processor 404, render the computer system 400 into a special-purpose machine that is customized to perform the operations specified in the instructions.

In an embodiment, the computer system 400 further includes a read only memory (ROM) 408 or other static storage device coupled to the bus 402 for storing static information and instructions for the processor 404. A storage device 410, such as a magnetic disk, optical disk, solid-state drive, or three-dimensional cross point memory is provided and coupled to the bus 402 for storing information and instructions.

In an embodiment, the computer system 400 is coupled via the bus 402 to a display 412, such as a cathode ray tube (CRT), a liquid crystal display (LCD), plasma display, light emitting diode (LED) display, or an organic light emitting diode (OLED) display for displaying information to a computer user. An input device 414, including alphanumeric and other keys, is coupled to bus 402 for communicating information and command selections to the processor 404. Another type of user input device is a cursor controller 416, such as a mouse, a trackball, a touch-enabled display, or cursor direction keys for communicating direction information and command selections to the processor 404 and for controlling cursor movement on the display 412. This input device typically has two degrees of freedom in two axes, a first axis (e.g., x-axis) and a second axis (e.g., y-axis), that allows the device to specify positions in a plane.

According to some embodiments, the techniques herein are performed by the computer system 400 in response to the processor 404 executing one or more sequences of one or more instructions contained in the main memory 406. Such instructions are read into the main memory 406 from another storage medium, such as the storage device 410. Execution of the sequences of instructions contained in the main memory 406 causes the processor 404 to perform the process steps described herein. In alternative embodiments, hard-wired circuitry is used in place of or in combination with software instructions.

The term "storage media" as used herein refers to any non-transitory media that store data and/or instructions that cause a machine to operate in a specific fashion. Such storage media includes non-volatile media and/or volatile media. Non-volatile media includes, for example, optical disks, magnetic disks, solid-state drives, or three-dimensional cross point memory, such as the storage device 410. Volatile media includes dynamic memory, such as the main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NV-RAM, or any other memory chip or cartridge.

Storage media is distinct from but may be used in conjunction with transmission media. Transmission media participates in transferring information between storage media. For example, transmission media includes coaxial cables, copper wire and fiber optics, including the wires that include the bus 402. Transmission media can also take the form of acoustic or light waves, such as those generated during radio-wave and infrared data communications.

In some embodiments, various forms of media are involved in carrying one or more sequences of one or more instructions to the processor 404 for execution. For example, the instructions are initially carried on a magnetic disk or solid-state drive of a remote computer. The remote computer loads the instructions into its dynamic memory and send the instructions over a telephone line using a modem. A modem local to the computer system 400 receives the data on the telephone line and use an infrared transmitter to convert the data to an infrared signal. An infrared detector receives the data carried in the infrared signal and appropriate circuitry places the data on the bus 402. The bus 402 carries the data to the main memory 406, from which processor 404 retrieves and executes the instructions. The instructions received by the main memory 406 may optionally be stored on the storage device 410 either before or after execution by processor 404.

The computer system 400 also includes a communication interface 418 coupled to the bus 402. The communication interface 418 provides a two-way data communication coupling to a network link 420 that is connected to a local network 422. For example, the communication interface 418 is an integrated service digital network (ISDN) card, cable modem, satellite modem, or a modem to provide a data communication connection to a corresponding type of telephone line. As another example, the communication interface 418 is a local area network (LAN) card to provide a data communication connection to a compatible LAN. In some implementations, wireless links are also implemented. In any such implementation, the communication interface 418 sends and receives electrical, electromagnetic, or optical signals that carry digital data streams representing various types of information.

The network link 420 typically provides data communication through one or more networks to other data devices. For example, the network link 420 provides a connection through the local network 422 to a host computer 424 or to a cloud data center or equipment operated by an Internet Service Provider (ISP) 426. The ISP 426 in turn provides data communication services through the world-wide packet data communication network now commonly referred to as the "Internet" 428. The local network 422 and Internet 428 both use electrical, electromagnetic, or optical signals that carry digital data streams. The signals through the various networks and the signals on the network link 420 and through the communication interface 418, which carry the digital data to and from the computer system 400, are example forms of transmission media. In an embodiment, the network 420 contains the cloud or a part of the cloud described above.

The computer system 400 sends messages and receives data, including program code, through the network(s), the network link 420, and the communication interface 418. In an embodiment, the computer system 400 receives code for processing. The received code is executed by the processor 404 as it is received, and/or stored in storage device 410, or other non-volatile storage for later execution.

Process for Providing Secure Medical Notifications

Figure 5:
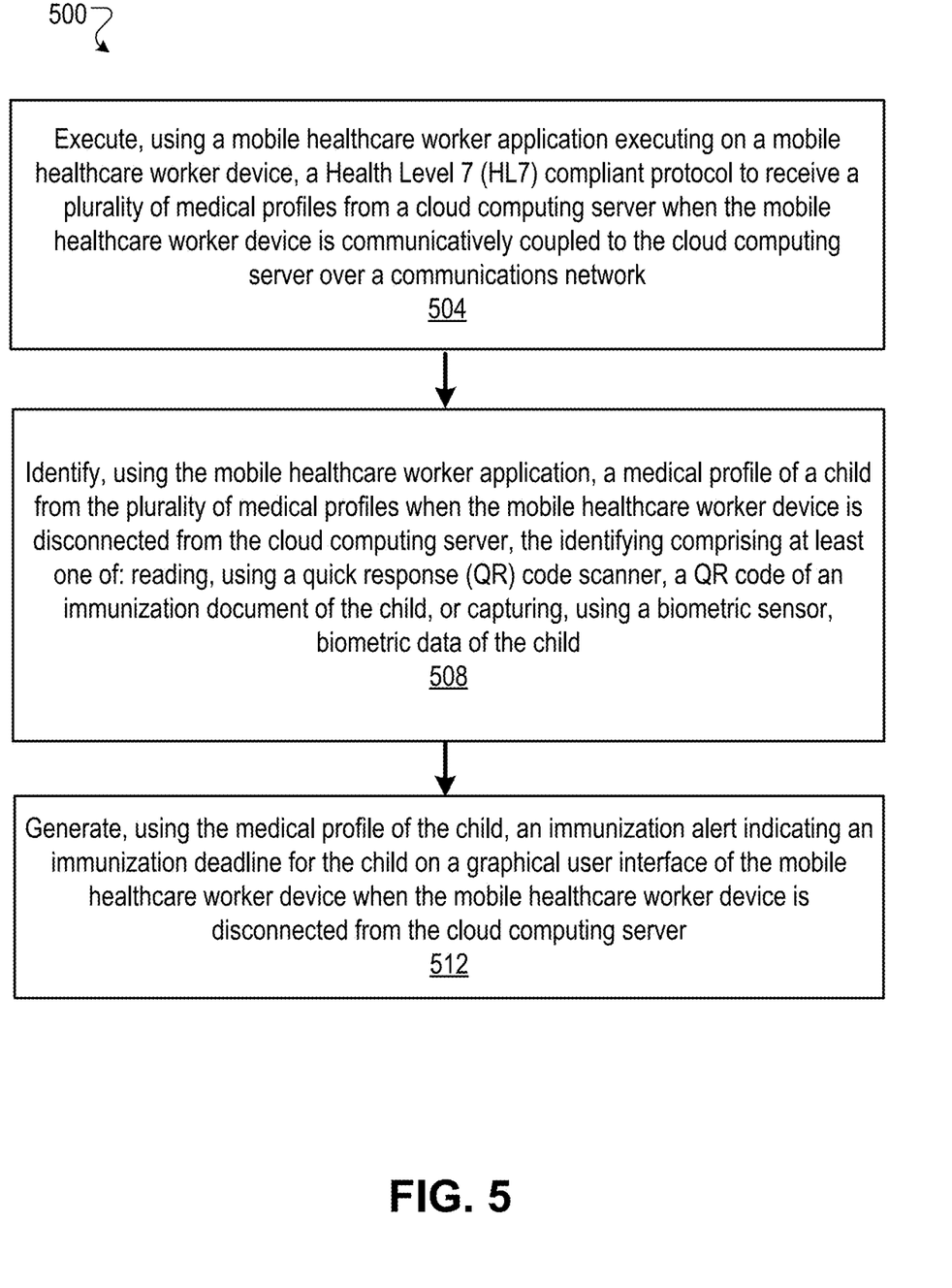
FIG. 5 illustrates a process for providing secure medical notifications using a cloud computing server in an online/offline mode.

FIG. 5 illustrates a process 500 for providing secure medical notifications using a cloud computing server 116 in an online/offline mode, in accordance with one or more embodiments. In some embodiments, the process 500 of FIG. 5 is performed by the mobile healthcare worker device 100. Other entities, for example, one or more components of the cloud computing server 116 perform some or all of the steps of the process 500 in other embodiments. Likewise, embodiments may include different and/or additional steps, or perform the steps in different orders.

The mobile healthcare worker application executes 504, on the mobile healthcare worker device 100, a Health Level 7 (HL7) compliant protocol to retrieve multiple medical profiles from a cloud computing server 116. All data at rest and in transit is encrypted. The mobile healthcare worker device 100 is communicatively coupled to the cloud computing server 116 over the communications network 104. The retrieve function is performed, e.g., when a healthcare worker visits a government location, healthcare center, or other location that has internet or cellular service. The HL7 compliant protocol is a messaging standard enabling electronic data exchange in the clinical domain and allows secure exchange of clinical data between central patient care systems, distributed environments where data resides in departmental systems, healthcare information technology vendors, and healthcare providers (e.g., the primary care provider device 108.

The mobile healthcare worker application identifies 508 a medical profile of a child from the retrieved medical profiles when the mobile healthcare worker device 100 is disconnected from the cloud computing server 116. The identifying includes at least one of reading, using a QR code scanner 144, a QR code of an immunization document of the child, or capturing, using a biometric sensor 140, biometric data of the child. In some embodiments, the biometric sensor 140 includes a camera configured to capture a fingerprint of the child or a fingerprint sensor configured to capture a fingerprint of the child. The camera or fingerprint sensor measures a physical difference between ridges and valleys of the fingerprint. For example, an optical fingerprint sensor projects the irregular 3D fingerprint onto a 2D flat plane in the captured fingerprint image.

The mobile healthcare worker application generates 512, using the medical profile of the child, an immunization alert 216 indicating an immunization deadline for the child on a graphical user interface 208 of the mobile healthcare worker device 100. In other embodiments, the mobile healthcare worker application generates an alert indicating a medical deadline for the child or a mother of the child. The mobile healthcare worker device 100 is disconnected from the cloud computing server 116 when generating the alert 216. The mobile healthcare worker application is thus configured to track progress of pregnancy of a mother and notify a healthcare worker or parent regarding a medical deadline for the child or a mother of the child based on registered birth information using, e.g., color codes for the alert 216 if a deadline is near. The mobile healthcare worker application also enables an administrative network to responsively update the deadlines. The operation of the mobile healthcare worker application is beneficial in geographical areas having lower internet or network coverage. For example, the immunization alert 216 indicates an immunization deadline (e.g., Feb. 11, 2019, as shown in FIG. 2) for the child on the graphical user interface 208 of the mobile healthcare worker device 100.

In the foregoing description, embodiments have been described with reference to numerous specific details that may vary from implementation to implementation. The description and drawings are, accordingly, to be regarded in an illustrative rather than a restrictive sense. The sole and exclusive indicator of the scope of the embodiments, and what is intended by the applicants to be the scope of the embodiments, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further including," in the foregoing description or following claims, what follows this phrase can be an additional step or entity, or a sub-step/sub-entity of a previously-recited step or entity.

What is claimed is:

1. A cloud computing system for providing secure medical alerts, comprising:
   a blockchain configured to store a plurality of medical profiles;
   a cloud computing server configured to store a cryptographic key, receive a request for the plurality of medical profiles stored in one or more blocks of the blockchain and provide the cryptographic key to access the plurality of medical profiles on the blockchain; and
   a mobile healthcare worker device associated with a first individual, comprising:
      a biometric sensor configured to capture biometric data of a patient, the patient being different from the first individual; and
      a mobile healthcare worker application configured to:
         execute a first protocol to retrieve the plurality of medical profiles, wherein retrieving the plurality of medical profiles causes an endorsement message to be sent to each of a plurality of devices of the blockchain;
         identify, using the biometric data, a medical profile of the patient from the plurality of medical profiles;
         generate, using the medical profile of the patient, an alert indicating a medical deadline for the patient or a family member of the patient on a graphical user interface of the mobile healthcare worker device, wherein data in a given block of the blockchain cannot be altered retroactively without altering subsequent blocks of the blockchain;
         identify an aggregate medical profile containing a health record of each individual related to the patient, the aggregate medical profile linked using a database entity link on the cloud computing server to the medical profile of the patient, the aggregate medical profile linked to the medical profile of the patient by a family number, a cellular phone number, an immunization card number, fingerprints, or a QR code;
         transmit the database entity link between the medical profile of the patient and the aggregate medical profile of individuals related to the patient, wherein the database entity link is a schema object in the medical profile of the patient;
         access the cryptographic key stored on the cloud computing server, the cryptographic key associated with a geographical area corresponding to the plurality of medical profiles; and retrieve, using the cryptographic key, the plurality of medical profiles from a peer-to-peer blockchain network, wherein the blockchain is managed by the peer-to-peer blockchain network adhering to a second protocol for inter-peer communication, the peer-to-peer blockchain network being configured to execute the inter-peer communication to validate new medical profiles added to the plurality of medical profiles.

2. The cloud computing system of claim 1, wherein the biometric sensor comprises at least one of:
a camera configured to capture a fingerprint of the patient;
a fingerprint sensor configured to capture the fingerprint of the patient;
a retina scanner configured to capture a retina scan of the patient; or
an iris scanner configured to capture an iris scan of the patient.

3. The cloud computing system of claim 1, wherein the mobile healthcare worker device further comprises a quick response (QR) code scanner configured to read a QR code of an immunization document of the patient.

4. The cloud computing system of claim 1, wherein the mobile healthcare worker application is further configured to:
generate, using the graphical user interface of the mobile healthcare worker device, the medical profile of the patient, the medical profile of the patient comprising demographic data and health data of the patient, wherein altering the subsequent blocks of the blockchain requires consensus of a majority of the devices of the blockchain.

5. The cloud computing system of claim 1, wherein the mobile healthcare worker application is further configured to initiate an audio-visual telemedicine session with a primary care provider application executing on a primary care provider device.

6. The cloud computing system of claim 1, wherein the mobile healthcare worker application is further configured to:
retrieve a record of a number of vaccinations and a type of the vaccinations in stock within the geographical area corresponding to the plurality of medical profiles when the mobile healthcare worker device is communicatively coupled to the cloud computing server over a communications network; and
generate, using the graphical user interface of the mobile healthcare worker device, a display of the record of the number of vaccinations and the type of the vaccinations, wherein a private key is stored in an enclave within the mobile healthcare worker device to generate a digital signature of the mobile healthcare worker device for security verification with the cloud computing server and the blockchain.

7. The cloud computing system of claim 1, further comprising a primary care provider application executing on a primary care provider device, the primary care provider application configured to:
identify a medical specialist corresponding to at least one of:
a medical condition of the patient; or
a medical condition of an individual related to the patient; and
transmit a database entity link between the medical specialist and the medical profile of the patient to the cloud computing server, wherein transmitting the database entity link causes a device of the blockchain to:
receive a prompt for a transaction to be performed on the medical profile of the patient;
sign an endorsement message using the cryptographic key; and
transmit the signed endorsement message to the cloud computing server.

8. A method for providing secure medical alerts, comprising:
executing, using a mobile healthcare worker application on a mobile healthcare worker device associated with a first individual, a first protocol to retrieve a plurality of medical profiles from a blockchain using a cryptographic key stored on a cloud computing server, the plurality of medical profiles stored in one or more blocks of the blockchain, wherein retrieving the plurality of medical profiles causes an endorsement message to be sent to each of a plurality of devices of the blockchain;
identifying, using the mobile healthcare worker application, a medical profile of a patient from the plurality of medical profiles, the patient being different from the first individual, the identifying comprising at least one of:
obtaining, using a quick response (QR) code scanner, a QR code of an immunization document of the patient; or
capturing, using a biometric sensor, biometric data of the patient;
generating, using the medical profile of the patient, an alert indicating a medical deadline for the patient or a family member of the patient on a graphical user interface of the mobile healthcare worker device, wherein data in a given block of the blockchain cannot be altered retroactively without altering subsequent blocks of the blockchain;
identifying an aggregate medical profile containing a health record of each individual related to the patient, the aggregate medical profile linked using a database entity link on the cloud computing server to the medical profile of the patient, the aggregate medical profile linked to the medical profile of the patient by a family number, a cellular phone number, an immunization card number, fingerprints, or a QR code;
transmitting the database entity link between the medical profile of the patient and the aggregate medical profile of individuals related to the patient, wherein the database entity link is a schema object in the medical profile of the patient;
storing, using a peer-to-peer blockchain network, the plurality of medical profiles, the peer-to-peer blockchain network being configured to execute inter-peer communication to validate new medical profiles added to the plurality of medical profiles, and wherein the blockchain is managed by the peer-to-peer blockchain network that adheres to a second protocol for inter-peer communication;
accessing, using the mobile healthcare worker application, the cryptographic key stored on the cloud computing server, the cryptographic key being associated with a geographical area corresponding to the plurality of medical profiles; and
retrieving, using the cryptographic key, the plurality of medical profiles from the peer-to-peer blockchain network.

9. The method of claim 8, wherein the biometric sensor comprises at least one of:
a camera configured to capture a fingerprint of the patient;
a fingerprint sensor configured to capture the fingerprint of the patient;

a retina scanner configured to capture a retina scan of the patient; or an iris scanner configured to capture an iris scan of the patient.

10. The method of claim 8, further comprising: generating, using the graphical user interface of the mobile healthcare worker device, the medical profile of the patient, the medical profile of the patient comprising demographic data and health data of the patient; and transmitting, using the mobile healthcare worker application, the database entity link between the medical profile of the patient and the aggregate medical profile of individuals related to the patient when the mobile healthcare worker device is communicatively coupled to the cloud computing server over a communications network, wherein altering the subsequent blocks of the blockchain requires consensus of a majority of the devices of the blockchain.

11. The method of claim 8, further comprising:
initiating, using the mobile healthcare worker application, an audio-visual telemedicine session with a primary care provider application executing on a primary care provider device.

12. The method of claim 8, further comprising:
retrieving, using the mobile healthcare worker application, a record of a number of vaccinations and a type of the vaccinations in stock within the geographical area corresponding to the plurality of medical profiles when the mobile healthcare worker device is communicatively coupled to the cloud computing server over a communications network; and
generating, using the graphical user interface of the mobile healthcare worker device, a display of the record of the number of vaccinations and the type of the vaccinations, wherein a private key is stored in an enclave within the mobile healthcare worker device to generate a digital signature of the mobile healthcare worker device for security verification with the cloud computing server and the blockchain.

13. The method of claim 8, further comprising:
identifying, using a primary care provider application executing on a primary care provider device, a medical specialist corresponding to at least one of:
a medical condition of the patient; or
a medical condition of an individual related to the patient;
receiving, using a device of the blockchain, a prompt for a transaction to be performed on the medical profile of the patient;
signing, using the device of the blockchain, an endorsement message using the cryptographic key; and
transmitting, using the device of the blockchain, the signed endorsement message to the cloud computing server.

14. One or more non-transitory storage media storing instructions which, when executed by one or more computer processors, cause the one or more computer processors to:
execute, using a mobile healthcare worker application on a mobile healthcare worker device associated with a first individual, a first protocol to retrieve a plurality of medical profiles of a blockchain and a cryptographic key to access the plurality of medical profiles, the cryptographic key stored on a cloud computing server, the plurality of medical profiles stored in one or more blocks of the blockchain, wherein retrieving the plurality of medical profiles causes an endorsement message to be sent to each of a plurality of devices of the blockchain;

identify, using the mobile healthcare worker application, a medical profile of a patient from the plurality of medical profiles, the patient being different from the first individual, the identifying comprising at least one of: obtaining, using a quick response (QR) code scanner, a QR code of an immunization document of the patient; or capturing, using a biometric sensor, biometric data of the patient;

generate, using the medical profile of the patient, an alert indicating a medical deadline for the patient or a family member of the patient on a graphical user interface of the mobile healthcare worker device, wherein data in a given block of the blockchain cannot be altered retroactively without altering subsequent blocks of the blockchain;

identify an aggregate medical profile containing a health record of each individual related to the patient, the aggregate medical profile linked using a database entity link on the cloud computing server to the medical profile of the patient, the aggregate medical profile linked to the medical profile of the patient by a family number, a cellular phone number, an immunization card number, fingerprints, or a QR code;

transmit the database entity link between the medical profile of the patient and the aggregate medical profile of individuals related to the patient, wherein the database entity link is a schema object in the medical profile of the patient;

store, using a peer-to-peer blockchain network, the plurality of medical profiles, the peer-to-peer blockchain network being configured to execute inter-peer communication to validate new medical profiles added to the plurality of medical profiles, and wherein the blockchain is managed by the peer-to-peer blockchain network that adheres to a second protocol for inter-peer communication;

access, using the mobile healthcare worker application, the cryptographic key stored on the cloud computing server, the cryptographic key being associated with a geographical area corresponding to the plurality of medical profiles; and retrieve, using the cryptographic key, the plurality of medical profiles from the peer-to-peer blockchain network.

15. The one or more non-transitory storage media of claim 14, wherein the biometric sensor comprises at least one of:
a fingerprint sensor configured to capture a fingerprint of the patient or the family member;
a retina scanner configured to capture a retina scan of the patient or the family member; or
an iris scanner configured to capture an iris scan of the patient or the family member.

16. The one or more non-transitory storage media of claim 14,
wherein the instructions when executed by the one or more computer processors further cause the one or more computer processors to:
generate, using the graphical user interface of the mobile healthcare worker device, the medical profile of the patient, the medical profile of the patient comprising demographic data and health data of the patient, wherein altering the subsequent blocks of the blockchain requires consensus of a majority of the devices of the blockchain.

17. The one or more non-transitory storage media of claim 14, wherein the instructions when executed by the one or more computer processors further cause the one or more computer processors to:
- initiate, using the mobile healthcare worker application, an audio-visual telemedicine session with a primary care provider application executing on a primary care provider device when the mobile healthcare worker device is communicatively coupled to the primary care provider device over a communications network;
- receive a prompt for a transaction to be performed on the medical profile of the patient;
- sign an endorsement message using the cryptographic key; and
- transmit the signed endorsement message to the cloud computing server.

* * * * *